United States Patent [19]
Pedain et al.

[11] Patent Number: 6,054,528
[45] Date of Patent: Apr. 25, 2000

[54] AQUEOUS COATING ADHESIVE AND SEALANT COMPOSITIONS CONTAINING OXADIAZOLINONES AND POLYAMINES

[75] Inventors: Josef Pedain, Köln; Klaus König, Odenthal; Peter Heitkämper, Dormagen; Manfred Schönfelder, Leverkusen, all of Germany

[73] Assignee: Bayer Aktiengesellschaft, Leverkusen, Germany

[21] Appl. No.: 09/118,244

[22] Filed: Jul. 17, 1998

[30] Foreign Application Priority Data

Jul. 24, 1997 [DE] Germany .................. 197 31 863

[51] Int. Cl.[7] .................. C08L 75/00; C08G 73/00; B32B 27/08; B32B 27/26; B32B 27/40
[52] U.S. Cl. .................. 524/839; 524/589; 524/800; 528/367; 528/368; 428/423.1
[58] Field of Search .................. 524/800, 839; 428/423.1; 528/367, 368

[56] References Cited

U.S. PATENT DOCUMENTS 3,585,200 6/1971 Sheppard et al. .................. 528/266
5,128,471 7/1992 Scholl .................. 544/222

FOREIGN PATENT DOCUMENTS 0 548 930 6/1993 European Pat. Off. .

OTHER PUBLICATIONS

Journal of the Chemical Society of Japan 1973, 10, pp. 1987–1992.
Chemical Abstracts, vol. 80, No. 16, Abstract No. 83693, XP–002091418.

*Primary Examiner*—Tae Yoon
*Attorney, Agent, or Firm*—Joseph C. Gil; Thomas W. Roy

[57] ABSTRACT

The present invention relates to aqueous compositions containing a) bis(1,3,4-oxadiazolin-5-ones) corresponding to formula (I)

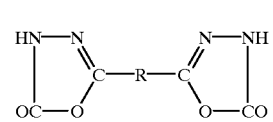

(I)

wherein

R represents a single bond or a divalent aliphatic, araliphatic or aromatic radical having 1 to 18 carbon atoms and b) organic polyamines or polyamine blends having an average of more than 2 NH— and/or $NH_2$— groups.

The present invention also relates to coatings, adhesives or sealants prepared from these aqueous compositions, in particular automotive clear coats.

5 Claims, No Drawings

AQUEOUS COATING ADHESIVE AND SEALANT COMPOSITIONS CONTAINING OXADIAZOLINONES AND POLYAMINES

BACKGROUND OF THE INVENTION

1. Field of the Invention

The present invention relates to aqueous compositions containing oxadiazolinones and polyamines, which cure at elevated temperatures to form cross-linked polymers coatings, adhesives and sealants.

2. Description of the Prior Art

Both one-component and two-component aqueous compositions are known. Examples include aqueous polyurethane dispersions and aqueous polymer emulsions and dispersions. They can be dried to form coatings and can under certain circumstances, e.g., with the addition of cross-linking hardeners, also cure to form water resistant and solvent resistant coatings. All of the known aqueous compositions of this type either have the disadvantage of a limited pot life when a cross-linking agent has been added, or have the disadvantage of releasing organic components contained within the cross-linking agent. For example, the blocking agent is liberated from blocked polyisocyanates during the cross-linking reaction. With regard to etherified melamine formaldehyde resins, which are also used on a large scale industrially, monoalcohols, among others, are released during cure.

A large number of commercial PUR dispersions contain tertiary amines or ammonia as neutralizing agents, which escape from the film as it dries or cures. This may result in pores forming as a film defect, and may cause give off an odor.

An object of the present invention is to avoid these disadvantages and provide aqueous, two-component cross-linkable compositions, which are stable at ambient temperatures of approximately 20 to 30° C. and which may be cross-linked at elevated temperatures to form a film without giving off volatile organic constituents from the film.

These objects may be achieved with the aqueous compositions containing oxadiazolinone derivatives and polyamines described hereinafter.

SUMMARY OF THE INVENTION

The present invention relates to aqueous compositions containing a) bis(1,3,4-oxadiazolin-5-ones) corresponding to formula (I)

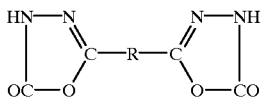

(I)

wherein

R represents a single bond or a divalent aliphatic, araliphatic or aromatic radical having 1 to 18 carbon atoms and b) organic polyamines or polyamine blends having an average of more than 2 NH— and/or $NH_2$— groups.

The present invention also relates to coatings, adhesives or sealants prepared from these aqueous compositions, in particular automotive clear coats.

DETAILED DESCRIPTION OF THE INVENTION

The starting products of formula (I) are known. Their preparation, e.g., from carboxylic acid hydrazides and phosgene, is described in the Journal of the Chemical Society of Japan 1973, 10, 1987–1992. This same reference also describes reactions between the compounds of formula (I) and diamines. However, because compounds (I) have high melting points and have extremely poor solubilities, the reactions are carried out at, for example, 160 to 300° C. in an evacuated tube or in a nitrogen stream.

The compounds of formula (I) can be dissolved in water together with polyamines and can be reacted at elevated temperature resulting in very valuable plastics and coatings. This is most surprising since compounds (I) are completely insoluble in water, and the polyamines are also either insoluble or only sparingly soluble in water. It is also surprising that the aqueous solutions of the compounds of formula (I) and polyamines form films at, e.g., 20 to 100° C. and above, despite the low molecular weights and high melting points of the substances.

In the formula (I) R preferably represents a single bond, the radical (—$CH_2$)$_n$—, wherein n is 1 to 18, or a bifunctional aromatic radical corresponding to formula (Ia),

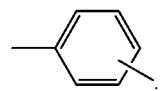

(Ia)

Example 1 describes the preparation of 1,4-bis(1,3,4-oxadiazolin-5-one-2-yl) butane, which is an example of the compounds which are preferably used.

The polyamines, including diamines, to be used according to the present invention are also known and obtainable in commercial quantities. The diamines and polyamines preferably have aliphatically bound amino groups. Triamines, such as diethylene triamine and nonane triamine, are preferred as well as reaction products of triols with acrylonitrile which may be converted in known manner into polyamines by hydrogenation of the nitrile groups. The polyamines prepared, for example, in accordance with DE-A 3,912,266 and 3,939,699 (U.S. Pat. No. 5,128,471, herein incorporated by reference) are also highly suitable.

Polyamines having an amino functionality of 3 or more can be used in admixture with diamines. Examples of diamines include hexamethylenediamine, isophorone diamine (IPDA) and 4,4'-diaminodicyclohexyl methane.

The ratio of compounds of formula (I) to polyamines may vary over a broad range. 0.5 to 5 NH— and/or $NH_2$— groups may be used for each 1,3,4-oxadiazoline group. As a result the properties of the cured plastics film may be varied within certain limits. Preferably 1 to 10, more preferably 2 to 3 NH— and/or $NH_2$— groups are used per compound of formula (I).

The aqueous mixtures of compounds of formula (I) with polyamines are clear solutions having a low viscosity and a solids content of 20 to 70%. They are colorless or pale yellow and have unlimited stability at up to approximately 40° C. When applied to a substrate, such as glass, they dry at above 50° C. to form clear, colorless, defect-free films which adhere very firmly to the substrate.

The aqueous solutions are for preparing coatings on a very wide variety of substrates, such as metal, glass, wood, textiles and leather. They can be blended with the known additives for coating compositions. They may also be used as adhesives or sealants due to their excellent adhesion properties.

A preferred application is for automotive coating, in particular for clear top coats.

The invention is further illustrated but is not intended to be limited by the following examples in which all parts and percentages are by weight unless otherwise specified.

EXAMPLES

Example 1

Preparation of 1,4-bis(1,3,4-oxadiazolin-5-one-2-yl) butane

A solution of 200 g of phosgene in 1.6 kg of phenol was introduced at 20° C. into a 4-liter phosgenation apparatus, and 174 g of adipic acid dihydrazide were added thereto. The mixture was heated to 85° C. within one hour, with stirring; gas evolved above a reaction temperature of 45° C. Phosgene was then introduced into the reaction mixture at 85° C. over 5 hours (approx. 30 g per hour), with stirring. The solution was then purged with nitrogen at 85 to 90° C. for 30 minutes, and the major part of the phenol was finally removed by vacuum distillation at from 50 to 60° C. The remaining product was dissolved in 1 liter of toluene at 60° C. and precipitated by cooling to 20° C. The precipitate was suction filtered, washed with toluene and dried under vacuum.

188 g (83% of theoretical yield) of colorless crystals having a melting point of 167–171° C. were obtained. After recrystallization from tetrahydrofuran, the melting point of the product was 171–172° C. The product is insoluble in water.

Example 2

Preparation of a polyamine

The procedure from Example 1 of DE-A 3,912,266 (U.S. Pat. No. 5,128,471) was repeated. A colorless polyamine having an amine nitrogen content of 7.8% was obtained by the formylation of a polyisocyanate, followed by the conversion of the resulting N-formyl groups into amino groups. The polyamine was highly viscous, or a solid-like wax under cold conditions, and was virtually insoluble in water.

Example 3

Preparation of a mixture according to the invention 454.5 g of the polyamine from Example 2 were stirred together with 453.5 g of water at approximately 60° C. Then 226 g of the product from Example 1 were added thereto at approximately 30° C. The mixture was stirred with a high-performance stirrer at high shear forces until a solution was formed. The latter solution was filtered in order to remove the slight turbidity. The resulting clear, pale yellowish aqueous solution had a solids content of approximately 60% and a viscosity of 250 mPa·s/23° C.

Example 4

Following the procedure of Example 3, a mixture was prepared from 226 g of substance from Example 1
359 g of polyamine from Example 2 and
586 g of water.

The resulting clear aqueous solution had a solids content of 50% and a viscosity of 180 mPa·s/23° C.

Example 5

Following the procedure of Example 3, a mixture was prepared from 226 g of substance from Example 1
430 g of substance from Example 2
23 g of hexamethylenediamine and
679 g of water.

The resulting clear aqueous solution had a solids content of approximately 50% and a viscosity of 200 mPa·s/23° C.

Example 6

The aqueous solutions from Examples 3 to 5 were applied to clean glass plates at a thickness of 120 μ with a coating knife and, after allowing the solvent to briefly evaporate, were cured within 30 minutes at 60° C., 80° C. and 100° C. Completely colorless films were obtained at all 3 temperatures. The films all remained unchanged after exposure to water and water/ethanol for 5 minutes. None of the specimens were scratched with a 5H pencil. The films, which were dried at 80 and 100° C., also showed no change on exposure to acetone.

This example demonstrates that two-dimensional plastics having excellent properties were obtained from the purely aqueous solutions according to the invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aqueous composition comprising
   a) a bis(1,3,4-oxadiazolin-5-one) corresponding to formula (I)

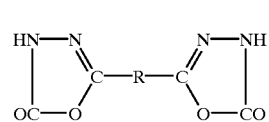

(I)

wherein
   R represents a single bond or a divalent aliphatic, araliphatic or aromatic radical having 1 to 18 carbon atoms and
   b) an organic polyamine or polyamine mixture having an average of more than 2 NH— and/or NH$_2$— groups.

2. The aqueous composition of claim 1 wherein R represents a divalent aliphatic radical.

3. A substrate coated with the aqueous composition of claim 1.

4. An automotive substrate coated with the aqueous composition of claim 1.

5. A substrate coated with a clear coating composition containing the aqueous composition of claim 1.

* * * * *